US009795332B2

(12) United States Patent
Abee

(10) Patent No.: US 9,795,332 B2
(45) Date of Patent: Oct. 24, 2017

(54) METHOD AND PULSE OXIMETER APPARATUS USING CHEMICAL HEATING

(71) Applicants: U.S. DEPARTMENT OF VETERANS AFFAIRS, Washington, DC (US); Catherine P. Abee, McKees Rocks, PA (US)

(72) Inventor: Catherine P. Abee, McKees Rocks, PA (US)

(73) Assignee: U.S. Department of Veterans Affairs, Washington, DC (US)

(*) Notice: Subject to any disclaimer, the term of this patent is extended or adjusted under 35 U.S.C. 154(b) by 212 days.

(21) Appl. No.: 14/361,047

(22) PCT Filed: Nov. 26, 2012

(86) PCT No.: PCT/US2012/066504
§ 371 (c)(1),
(2) Date: May 28, 2014

(87) PCT Pub. No.: WO2013/081956
PCT Pub. Date: Jun. 6, 2013

(65) Prior Publication Data
US 2014/0336483 A1    Nov. 13, 2014

Related U.S. Application Data

(60) Provisional application No. 61/629,825, filed on Nov. 29, 2011.

(51) Int. Cl.
*A61B 5/1455* (2006.01)
*A61B 5/1491* (2006.01)
*A61B 5/00* (2006.01)

(52) U.S. Cl.
CPC ........ *A61B 5/1491* (2013.01); *A61B 5/14551* (2013.01); *A61B 5/14552* (2013.01); *A61B 5/6831* (2013.01)

(58) Field of Classification Search
None
See application file for complete search history.

(56) References Cited

U.S. PATENT DOCUMENTS

| 4,825,879 A | 5/1989 | Tan et al. |
| 4,926,867 A | 5/1990 | Kanda et al. |

(Continued)

FOREIGN PATENT DOCUMENTS

| EP | 1538969 A | 6/2005 |
| WO | WO 2004/010867 A1 | 2/2004 |

(Continued)

OTHER PUBLICATIONS

PCT International Search Report and the Written Opinion dated Feb. 8, 2013, in International Appl. No. PCT/US2012/066504, filed Nov. 26, 2012 (9 pp).

(Continued)

*Primary Examiner* — Eric Winakur
*Assistant Examiner* — Marjan Fardanesh
(74) *Attorney, Agent, or Firm* — Dinesh Agarwal, P.C.

(57) ABSTRACT

Method and apparatus for providing reliable blood oxygen (SaO2) and heart rate measurements includes a chemical energy heating source in conjunction with a harness that is adapted to secure the chemical energy heating source and a pulse oximeter probe proximate to a region of the body which is to be warmed prior to measurement. Preferably, the chemical energy heating source is in the form a mixture including a metal powder, which releases heat at a predetermined rate via oxidation of the metal powder when exposed to the atmosphere. The apparatus may be designed to be reusable or disposable and can be used in a transmission or reflectance mode, or both.

14 Claims, 14 Drawing Sheets

(56) References Cited

U.S. PATENT DOCUMENTS

| | | | |
|---|---|---|---|
| 5,131,391 | A | 7/1992 | Sakai et al. |
| 6,343,223 | B1 | 1/2002 | Chin et al. |
| 6,385,821 | B1 | 5/2002 | Modgil et al. |
| 6,466,808 | B1 | 10/2002 | Chin et al. |
| 6,731,963 | B2 | 5/2004 | Finarov et al. |
| 6,839,579 | B1 | 1/2005 | Chin |
| 7,650,177 | B2 | 1/2010 | Hoarau et al. |
| 7,869,850 | B2 | 1/2011 | Hoarau et al. |
| 2002/0077535 | A1 | 6/2002 | Finarov et al. |
| 2003/0040783 | A1 | 2/2003 | Salmon |
| 2005/0101851 | A1 | 5/2005 | Chin |
| 2005/0209516 | A1 | 9/2005 | Fraden |
| 2006/0135016 | A1 | 6/2006 | Iwasaki |
| 2009/0105605 | A1 | 4/2009 | Abreu |
| 2009/0156914 | A1 | 6/2009 | O'Neil et al. |
| 2010/0049007 | A1 | 2/2010 | Sterling et al. |
| 2011/0196211 | A1 | 8/2011 | Al-Ali et al. |
| 2013/0096405 | A1 | 4/2013 | Garfio |

FOREIGN PATENT DOCUMENTS

| | | |
|---|---|---|
| WO | WO 2005/010568 A2 | 2/2005 |
| WO | WO 2009/032074 A1 | 3/2009 |

OTHER PUBLICATIONS

HeatMax—Material Safety Data Sheet. Version: Jan. 7, 2008 (3 pp).
Russell, MW. Another Look at the Forehead Sensor. http://www.apsf.org/newsletters/html/2004/fall/03forehead.htm, (2 pgs.) (Accessed Jun. 29, 2012).
Reynolds, LM et al. Influence of Sensor Site Location on Pulse Oximetry Kinetics in Children. Anesth Analg 1993;76:751-754.
European Search Report dated Jan. 28, 2016, in European Patent Application 12852610.0 (8 pp).

METHOD AND PULSE OXIMETER APPARATUS USING CHEMICAL HEATING

CROSS-REFERENCE TO RELATED APPLICATIONS

The present application claims priority on prior U.S. Provisional Application Ser. No. 61/629,825, filed Nov. 29, 2011, which is hereby incorporated herein in its entirety by reference.

FIELD AND BACKGROUND OF THE INVENTION

The present invention is generally directed to non-invasive medical procedures for measuring a person's (or animal's) blood-related signals, and more particularly to a method and pulse oximeter apparatus for measuring blood-oxygen levels that uses chemical heating.

Pulse oximetry is a procedure used to monitor blood arterial oxygen saturation ($SaO_2$) levels and pulse rates noninvasively. Pulse oximetry is used in operating rooms, ICU, during emergency transport, etc.

Currently, there are two modes of pulse oximetry sensor configurations: the transmission mode and the reflectance mode. The transmission mode often is used when a pulse oximeter probe is placed on the finger, ear lobe or toe. This mode uses an optical emitter and a detector positioned on opposite sides of the tissue through which the measurement is to be made. The reflectance mode often is used on the forehead and the optical emitter and the detector are positioned side by side. In both types, the pulse oximeter probes transmit red and infrared light through blood-perfused tissue, for example, the arterial vascular bed. The detector measures the transmitted light as it passes through the vascular bed, thereby detecting the amount of colored light absorbed by the arterial blood, and from this the arterial oxygen saturation level is calculated.

While pulse oximetry has become a standard for measuring oxygen saturation, there are number of situations where it performs poorly. For example, variations in the tissue temperature in the region of the measurement site can affect the accuracy of the measurements by affecting blood perfusion. Low tissue temperatures result in vasoconstriction and low blood perfusion, which make it difficult to obtain valid $SaO_2$ pulse rate values. The inability to obtain accurate $SaO_2$ and pulse readings can lead to misdiagnosis, incorrect treatment, or procedures to be canceled. $SaO_2$ and pulse readings are important to maintain patient stability during diagnostic testing, surgical procedures and monitoring, while in critical care areas. Changes in $SaO_2$ and pulse rate are important to monitor in order to be able to compensate for any decrease in patient oxygen saturations during hemodynamic monitoring.

Various methods have been tried over the years for increasing the measurement site tissue temperature in conjunction with pulse oximetry measurements. Some of these methods are described in the following patent documents: U.S. Pat. No. 4,926,867 to Kanda et al., U.S. Pat. No. 5,131,391 to Sakai et al., U.S. Pat. No. 6,343,223 B1 to Chin et al., U.S. Pat. No. 6,466,808 B1 to Chin et al., U.S. Pat. No. 6,839,579 B1 to Chin; U.S. Patent Application Publication Nos. 2003/0040783 A1 to Salmon, 2005/0101851 A1 to Chin, 2005/0209516 A1 to Fraden; European Patent No. EP 1 538969 B1 to Welsch Allyn, Inc.; and PCT International Pub. No. WO 2009/032074 A 1 to Woolsthorpe, LLC (the '074 application). In most of these methods, the heat is applied by the use of an electrical heating source.

However, the '074 application goes further and describes the use of any "heating means", which it defines as including "any means of increasing the core or tissue temperature of a subject, including, without limitation, one or more (i.e., in combination of) devices that transmit heat energy, such as thermoelectric heating devices (e.g., heating elements of various sizes, shapes, materials, etc. that are adapted to cooperate with various heating apparatus and/or configurations, such as a heated glove), contact heaters, lamps, heating blankets, etc., heated rooms, heated liquids, devices that transmit ultrasonic or photoelectric energy, and mentholated, counterirritant and/or vasodilating substances . . . [and] also means includes passive heating means, i.e., means for limiting heat from escaping a specific tissue region of the body." The '074 application emphasizes the application of heat over a large tissue region, such as an entire organ, appendage, or the entire body, but also notes that the heat can be applied to smaller regions, e.g., a single finger in conjunction with obtaining a pulse oximeter reading on the finger. It also teaches the optional use of sensors to monitor the skin temperature during heating.

Various other sensors/monitors are disclosed in U.S. Pat. No. 6,385,821 to Modgil et al, U.S. Pat. No. 6,731,963 to Finarov et al., U.S. Pat. No. 7,650,177 to Hoarau et al., U.S. Pat. No. 7,869,850 to Hoarau et al., and PCT International Pub. No. WO 2005/010568.

Nonetheless, an improved pulse oximeter probe can be envisioned which includes self-contained non-electric heating means.

ASPECTS AND BRIEF SUMMARY OF THE INVENTION

The present disclosure is directed to various aspects of the present invention.

One aspect of the present invention is to provide a method and apparatus for non-invasive measurement of a patient's blood oxygen level ($SaO_2$) and/or pulse rate with enhanced reliability and accuracy.

Another aspect of the present invention is to provide a method and pulse oximeter apparatus which utilizes chemical heating for warming the region of the measurement site.

Another aspect of the present invention is to provide a method and pulse oximeter apparatus which includes a chemical heating means in the form of a metal mixture.

Another aspect of the present invention is to provide a method and pulse oximeter apparatus which includes a self-contained chemical heating means in the form of a metal mixture that may optionally be of a single-use type which is disposable.

Another aspect of the present invention is to provide a method and pulse oximeter apparatus which includes a self-heated pulse oximeter probe that may optionally be of a single-use type which is disposable.

Another aspect of the present invention is to provide a method and pulse oximeter apparatus which includes a pulse oximeter probe that is of a transmission type, reflectance type, or both.

Another aspect of the present invention is to provide a pulse oximeter apparatus, which includes a harness including first and second sections, a probe operably secured to the harness, wherein one of the first and second sections includes a pocket for accommodating a source of chemical heating and is made of an air permeable material so as to allow the air to come in contact with the chemical heating source and release heat.

Another aspect of the present invention is to provide a pulse oximeter apparatus, which includes a flexible harness including first and second sections joined by a bridge section, a probe operably secured to the harness and including a lead for transmitting a signal to a processor, wherein the harness is adapted to hold the probe in a fixed position to a portion of the body and includes a pocket in one of the first and second sections thereof. The pocket is adapted to accommodate a source of chemical heating therein. The pocket holding section of the harness is made of an air permeable material so as to allow the air to come in contact with the chemical heating source and release heat.

Another aspect of the present invention is to provide a non-invasive method of measuring a blood oxygen level ($SaO_2$) or pulse rate of a subject, which includes providing a self-heated pulse oximeter apparatus, including i) a harness having first and second sections, ii) a probe operably secured to the harness, iii) one of the first and second sections including a pocket for accommodating a source of chemical heating and being made of an air permeable material so as to allow the air to come in contact with the chemical heating source and release heat. The chemical heating source is exposed to air, and the pulse oximeter apparatus is positioned at a measurement site on the subject for a predetermined time period to take the measurements.

Another aspect of the present invention is to provide a non-invasive method of measuring a blood oxygen level ($SaO_2$) or pulse rate of a subject, which includes providing a self-heated pulse oximeter apparatus, including i) a flexible harness including first and second sections joined by a bridge section, ii) a probe operably secured to the harness and including a lead for transmitting a signal to a processor, iii) the harness being adapted to hold the probe in a fixed position relative to a portion of the body and including a pocket in one of the first and second sections thereof, which pocket is adapted to accommodate a source of chemical heating therein. One of the first and second sections is made of an air permeable material so as to allow the air to come in contact with the chemical heating source therein and release heat. The chemical heating source is exposed to air and the pulse oximeter apparatus is positioned at a measurement site on the subject for a predetermined time period to take the measurements.

In summary, the present invention provides a novel apparatus and method for providing reliable pulse oximeter measurements of $SaO_2$ and heart rate. The inventive apparatus comprises a pulse oximeter probe integrated into a bandage-like harness, which contains a chemical energy heating source and is adapted to reversibly secure the heating source and the pulse oximeter probe proximate to the body region at which the pulse oximeter measurement is to be made.

For simplicity of expression, embodiments of the inventive apparatus are referred to hereinafter by the term "self-heated pulse oximeter probe". It is to be understood that the term "pulse oximeter probe" when used apart from the term "self-heated pulse oximeter probe" is meant to refer to the combination of light source and receptor that generate the signals which are used to calculate the $SaO_2$ and/or heart rate values.

The pulse oximeter probe portion of the self-heated pulse oximeter probe may be configured for the transmission mode or the reflectance mode, or for both.

Preferably, the chemical energy source is in the form of a mixture that includes a metal powder, which generates heat energy at a predetermined rate via oxidation of the metal powder when the metal powder is exposed to the atmosphere. In some embodiments, the self-heated pulse oximeter probe is designed to be used once and then disposed of, but in other embodiments, it is designed to be reusable upon replacement of the chemical energy heating source.

BRIEF DESCRIPTION OF THE DRAWINGS

One of the above and other aspects, novel features and advantages of the present invention will become apparent from the following detailed description of the non-limiting preferred embodiment(s) of invention, illustrated in the accompanying drawings, wherein.

DETAILED DESCRIPTION OF THE PREFERRED EMBODIMENT(S) OF THE INVENTION

A few preferred embodiments of the present invention are described in detail sufficient for one skilled in the art to practice the present invention. It is understood, however, that the fact that a limited number of preferred embodiments are described herein does not in any way limit the scope of the present invention.

Figure 1:
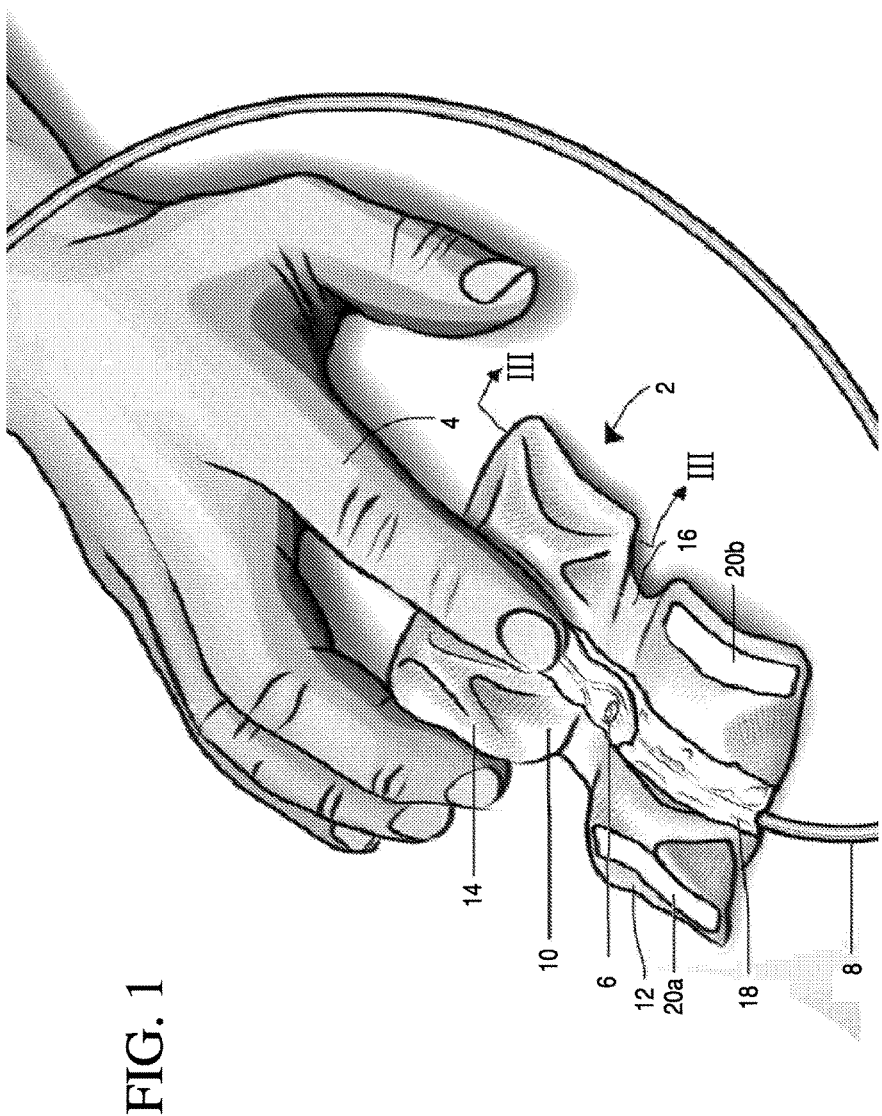
FIG. 1 is a schematic perspective view of a self-heated pulse oximeter probe, according to a first embodiment of the present invention, shown in an open position being secured onto a person's index finger to measure $SaO_2$.

Referring to FIG. 1, a self-heated pulse oximeter probe 2, according to a first embodiment of the present invention, is shown in an open position, as it is being applied to measure $SaO_2$ on a person's index finger 4. The self-heated pulse oximeter probe 2 includes a pulse oximeter probe 6, which has a lead 8 that is adapted to transmit signals from the pulse oximeter probe 6 to a data collection and processing unit (not shown). It is noted that in the embodiment shown, the pulse oximeter probe 6 is of a transmission type, and only the optical emitter portion is visible in FIG. 1, the detector portion being located beneath and hidden by the finger 4.

The self-heated pulse oximeter probe 2 also includes a flexible harness 10 having first and second wings 12 and 14, connected by a flexible bridge 16.

The harness 10 is configured to wrap around and become removably attached to the finger 4. The harness 10 includes at least one fastener 18 located on the inner side of the wing 12, for holding the oximeter probe 6 in place relative to the harness 10. Although the fastener 18 is shown to be a sleeve-type fastener, any other suitable releasable or permanent fastener may be used. It is preferred, however, that the fastener 18 be releasable so that the pulse oximeter probe 6 may be removed for reuse in cases where the self-heated oximeter probe 2 is designed to be disposable.

Figure 2:
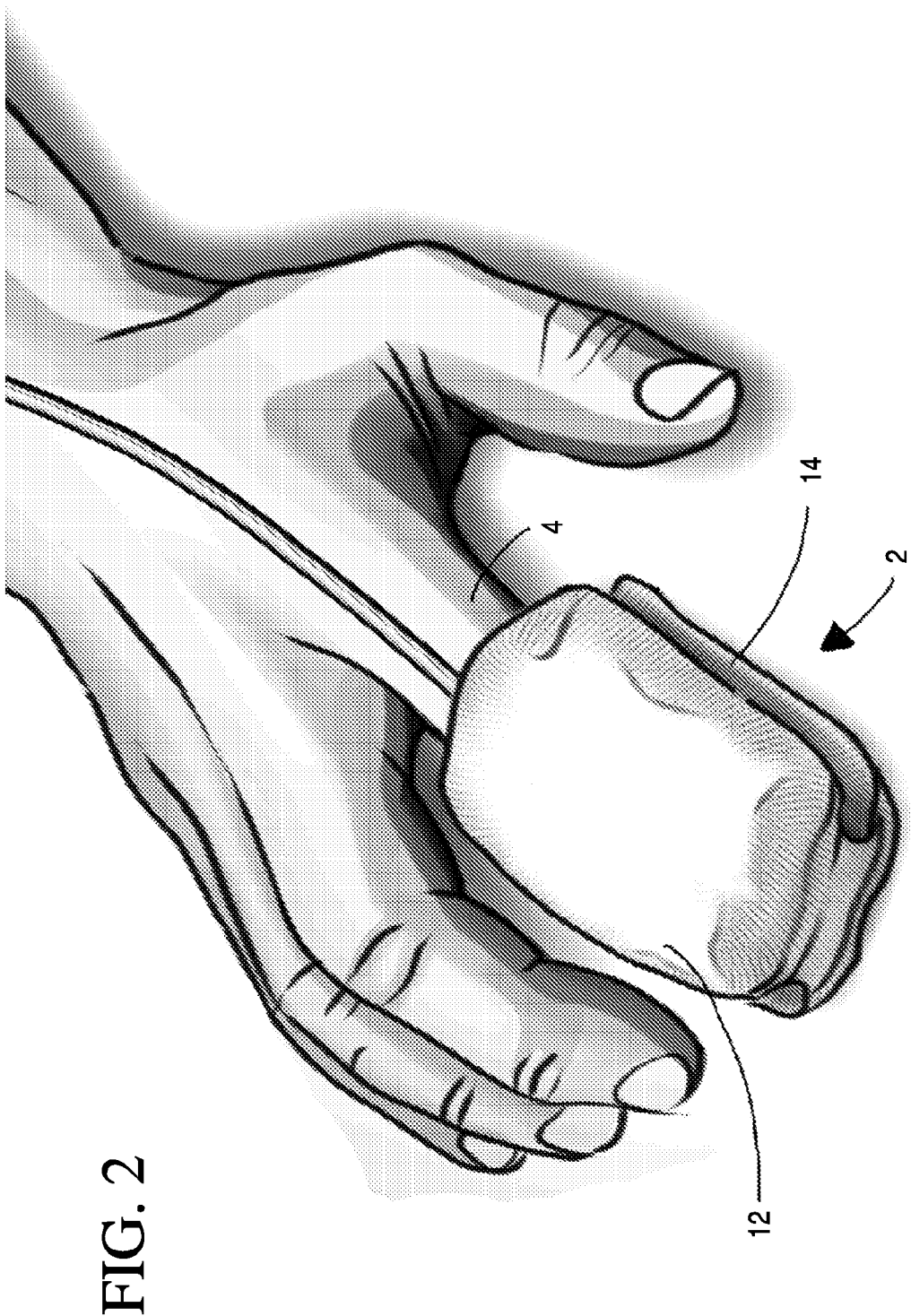
FIG. 2 is a schematic perspective view of the embodiment depicted in FIG. 1, shown in a closed operating position on the person's index finger.

The harness 10 also includes adhesive strips 20a and 20b, located on the inner side of wing 12, which are adapted to removably adhere to the inner side of wing 14, when the harness 10 is in the closed position, as shown in FIG. 2.

Figure 3:
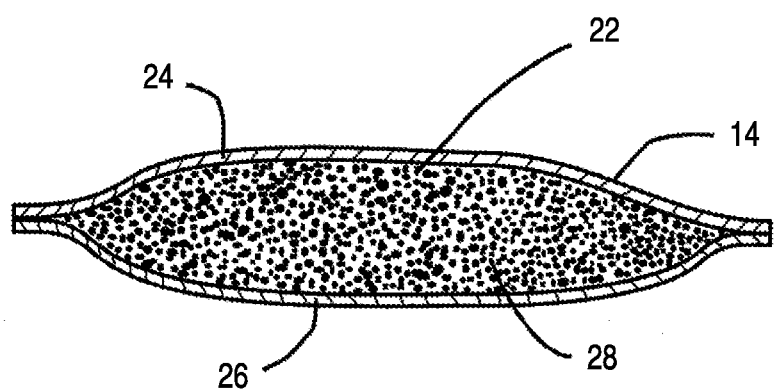
FIG. 3 is an enlarged cross-sectional view taken along line III-III of FIG. 1.

The harness 10 further includes, within one or both wings 12 and 14, one or more internal pockets which contain a chemical energy heating source for heating the finger 4 prior to and during the measurement of the person's $SaO_2$ and/or pulse rate. One such pocket is depicted in FIG. 3, which shows a cross-section of wing 14 taken along line III-III of FIG. 1. The pocket 22 is defined by inner and outer sides 24 and 26 of wing 14, and contains a chemical energy heating source 28, which is described in more detail hereinafter.

It is understood that although the pocket 22, shown in this embodiment, permanently contains a chemical heating source 28, it is also within the contemplation/scope of the present invention that pockets, such as pocket 22, be configured to have one or more openings through which a chemical heating source may be placed within or removed from the pocket, thus making the self-heated pulse oximeter probe reusable.

Figure 4:
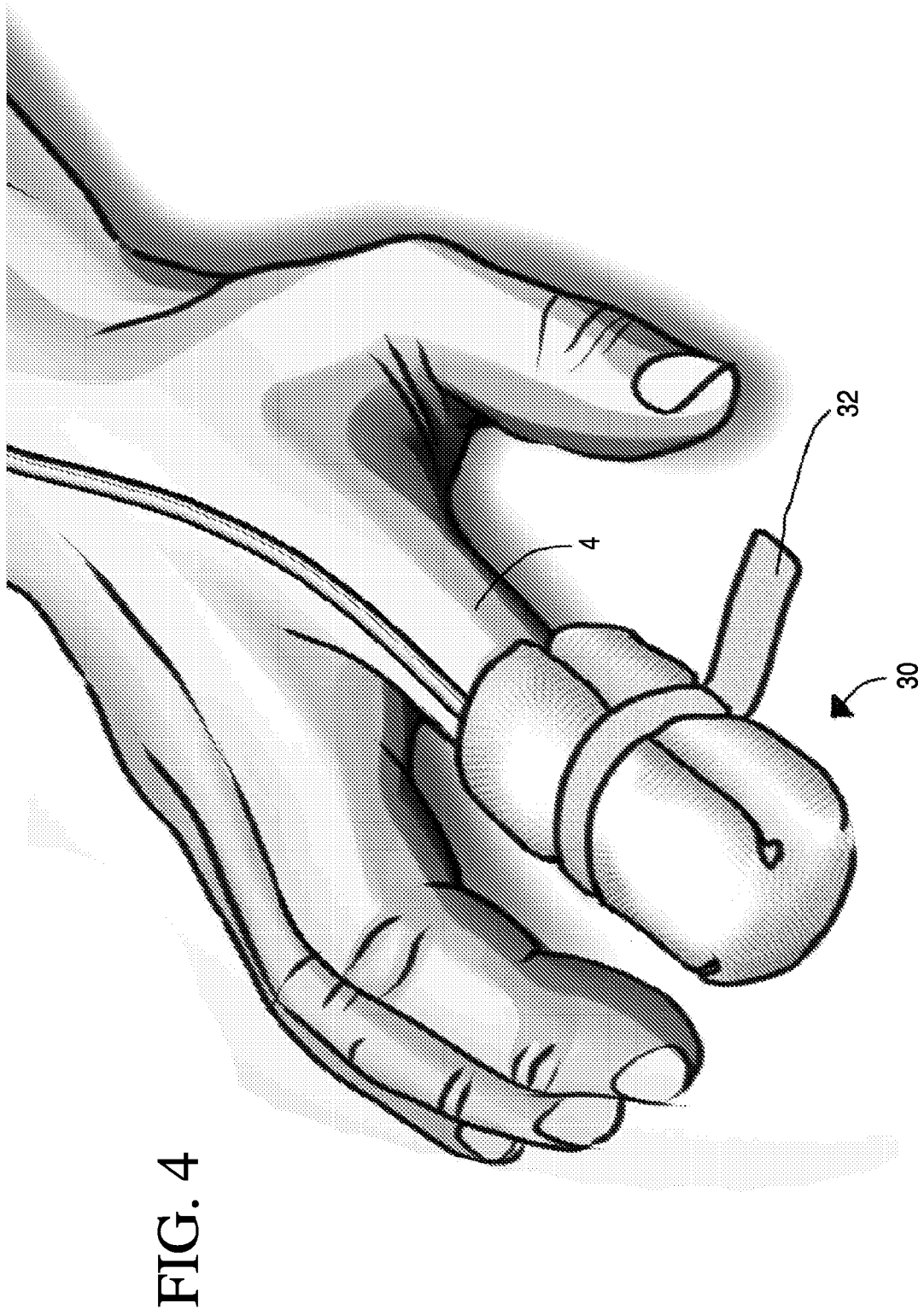
FIG. 4 is a schematic perspective view showing a self-heated pulse oximeter probe, according to a second embodiment of the present invention, shown in a closed operating position on a person's index finger.
Figure 5:
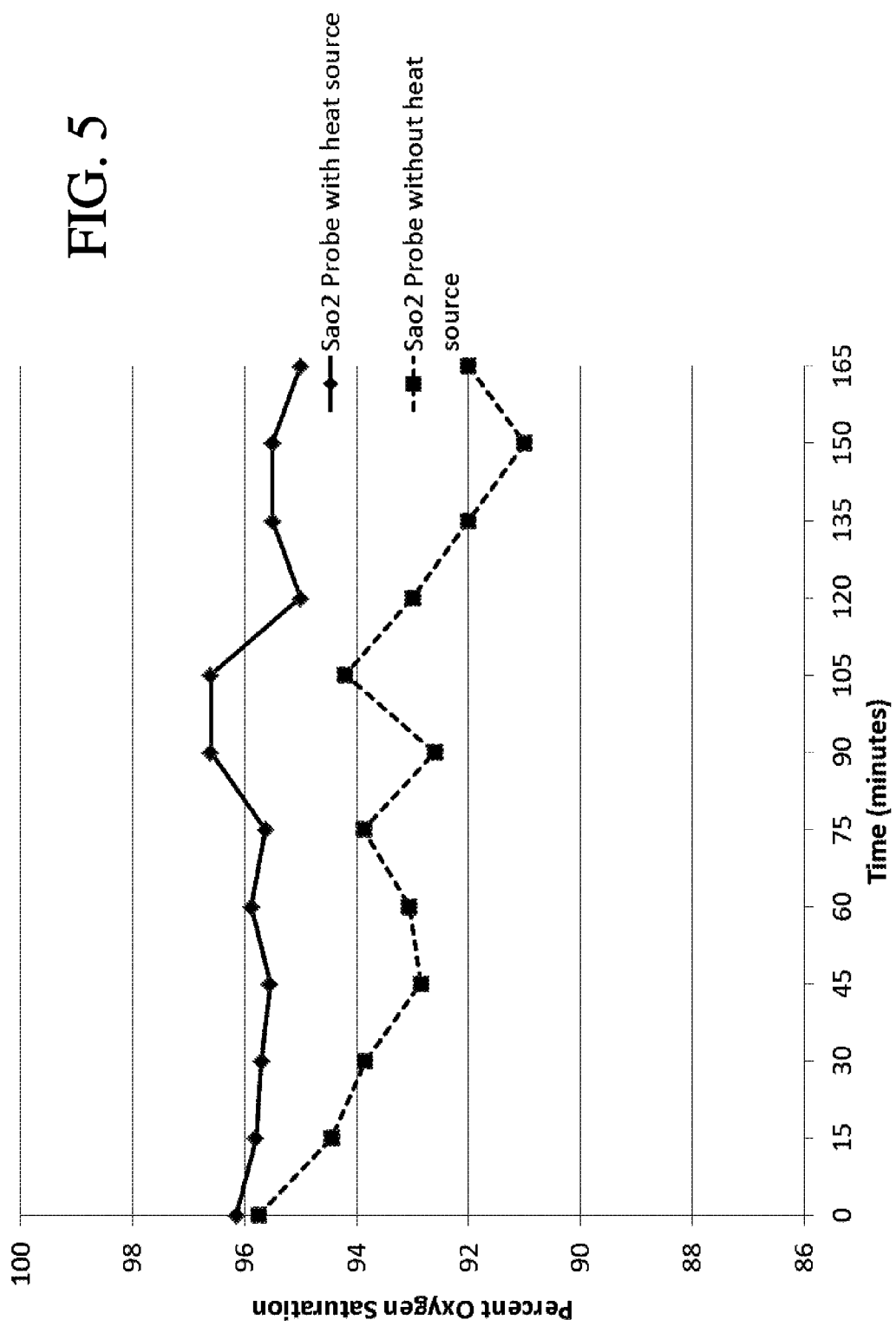
FIG. 5 is a graphical illustration of average $SaO_2$ readings for control subjects.
Figure 6:
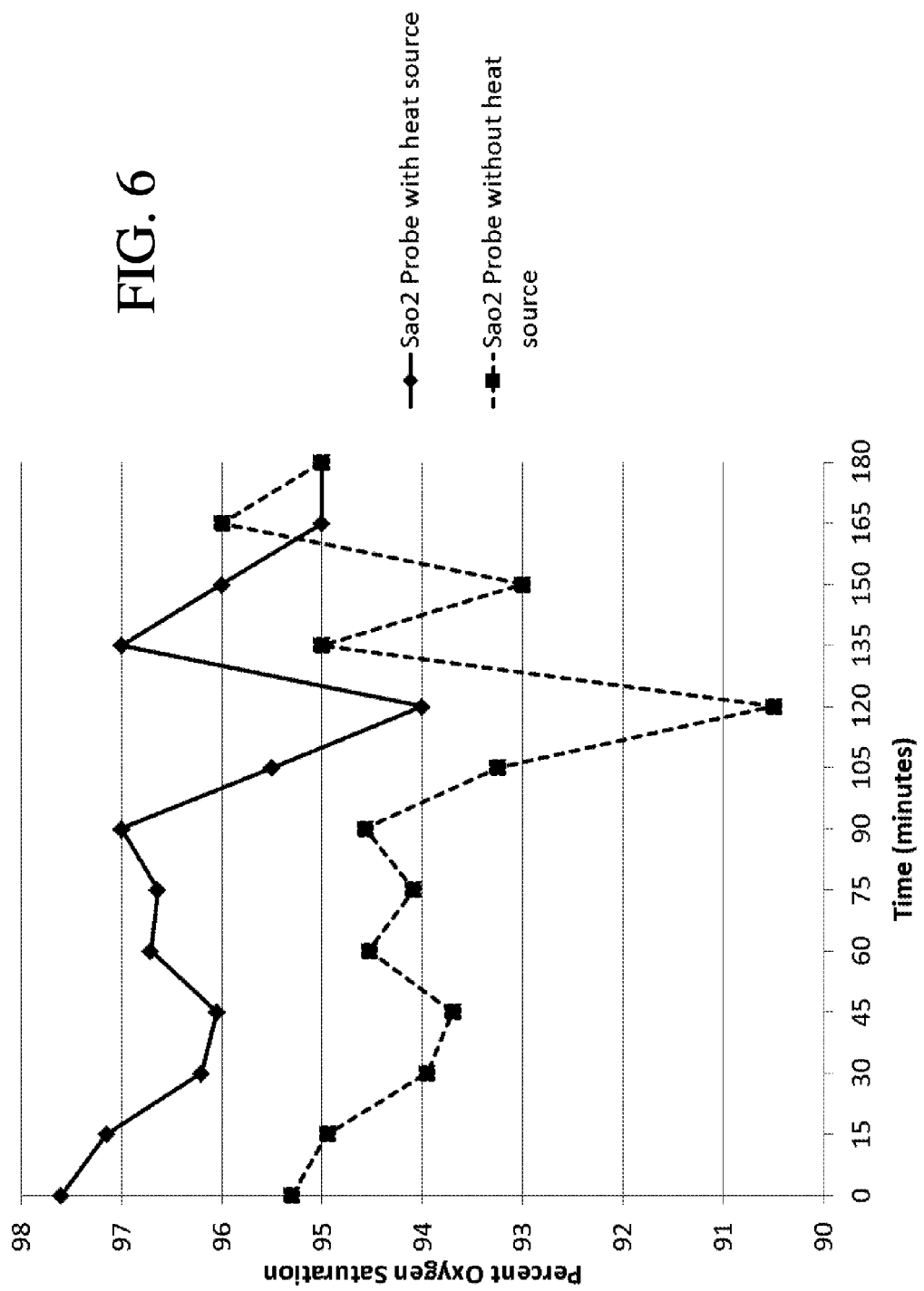
FIG. 6 is a graphical illustration of average $SaO_2$ readings for test subjects.
Figure 7:
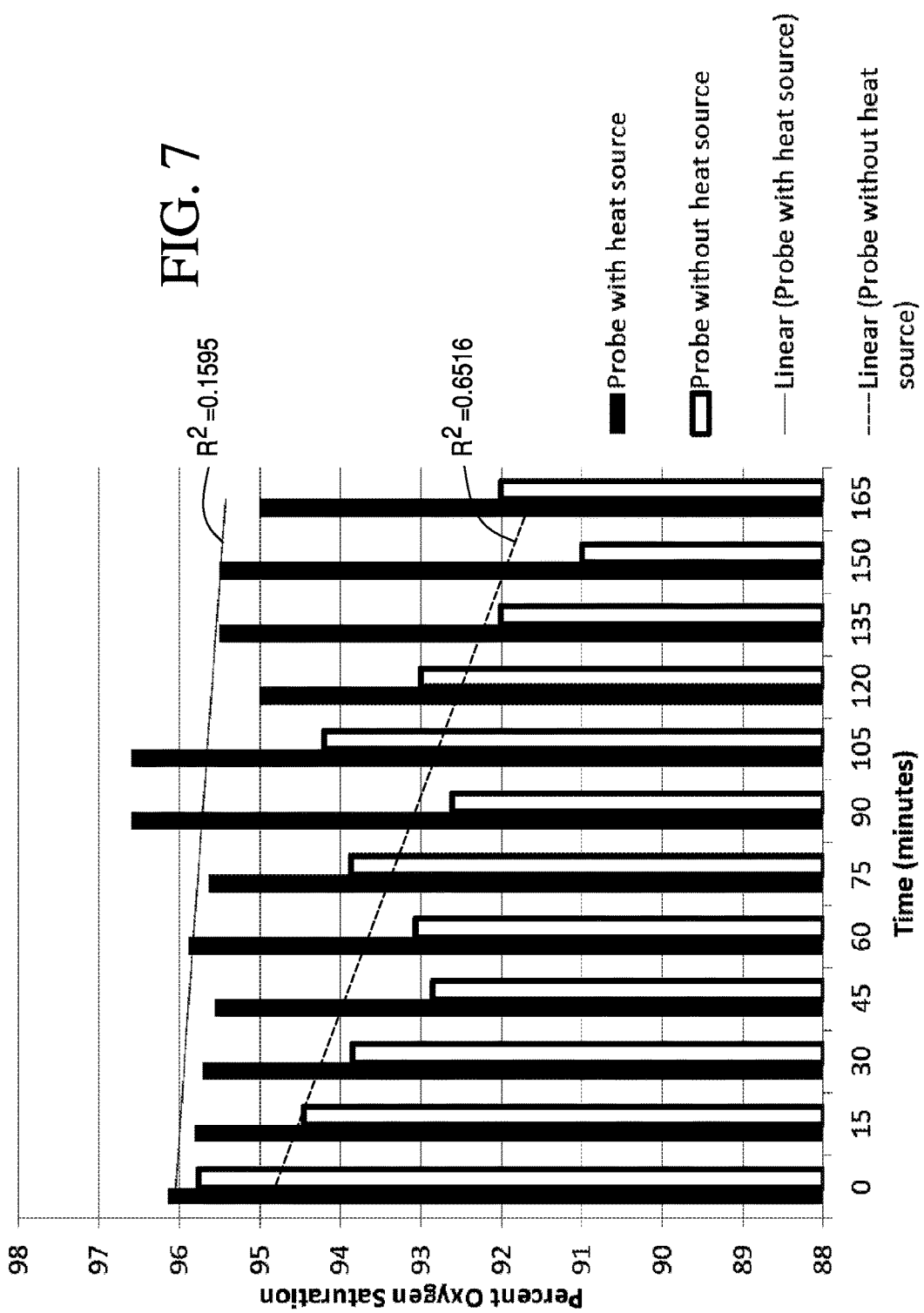
FIG. 7 is a bar chart comparing $SaO_2$ in control subjects.
Figure 8:
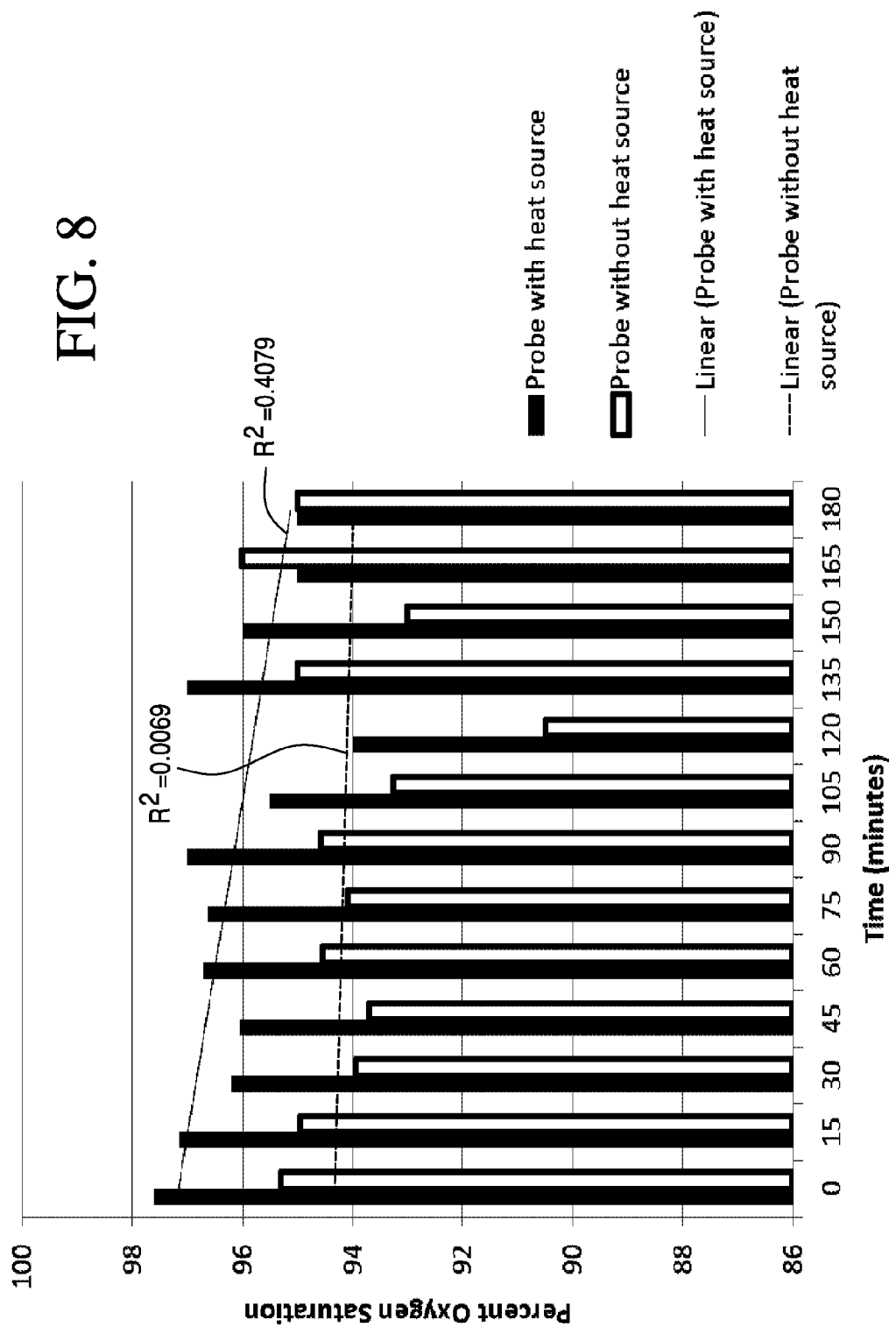
FIG. 8 is a bar chart comparing $SaO_2$ in test subjects.
Figure 9:
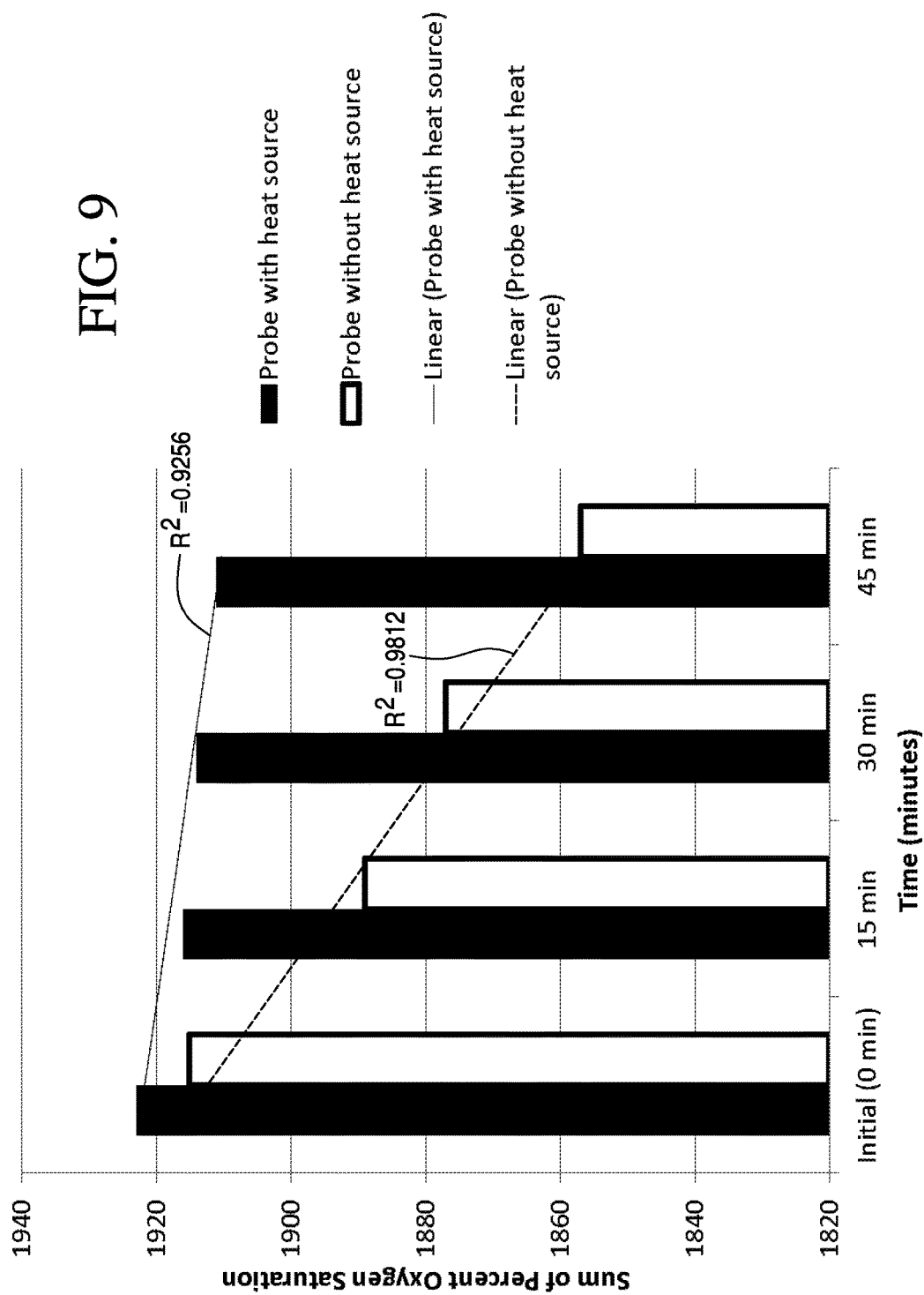
FIG. 9 is a bar chart illustrating $SaO_2$ raw data in control subjects for first 45 minutes (n=20)
Figure 10:
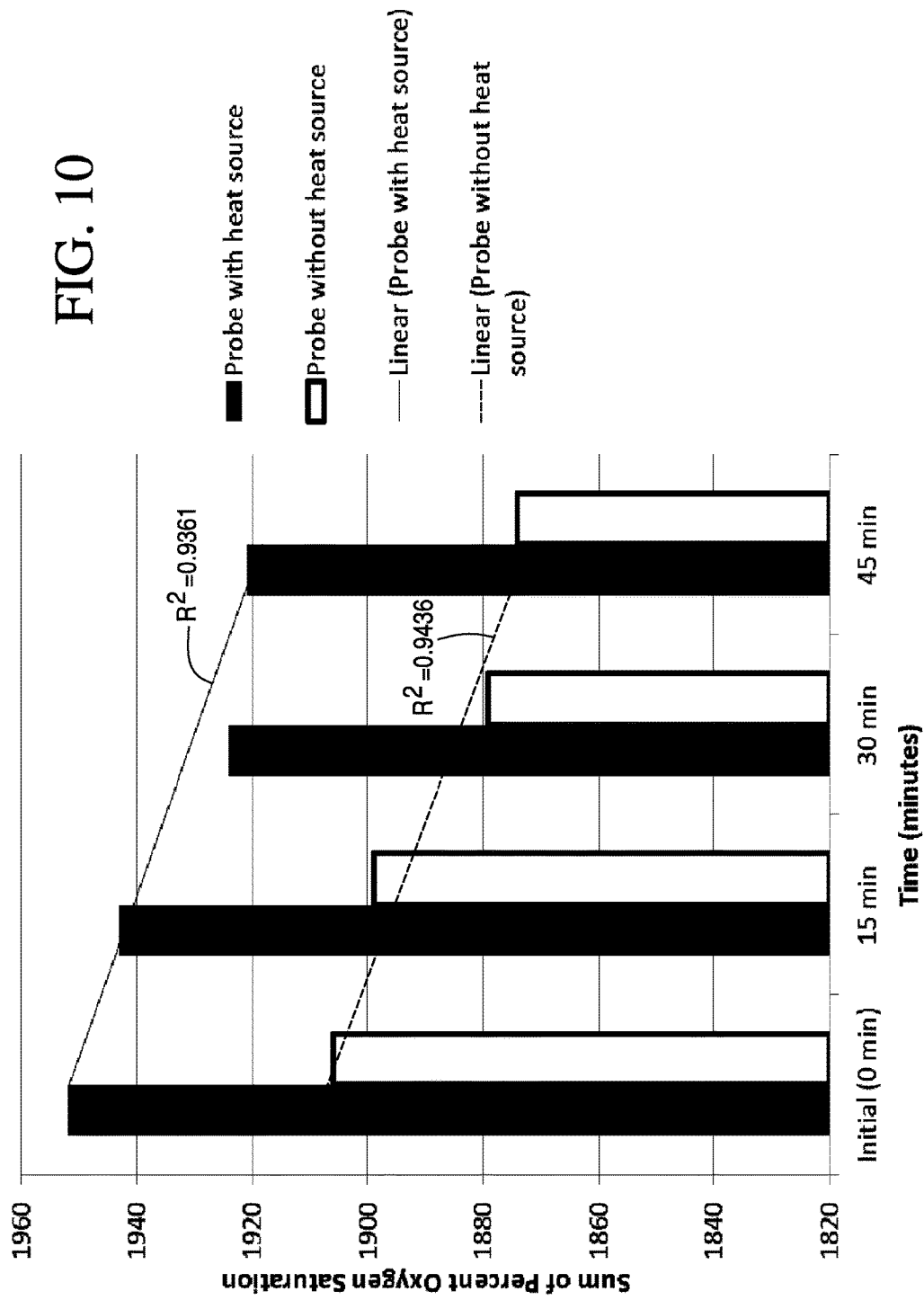
FIG. 10 is a bar chart illustrating $SaO_2$ raw data in test subjects for first 45 minutes (n=20)
Figure 11:
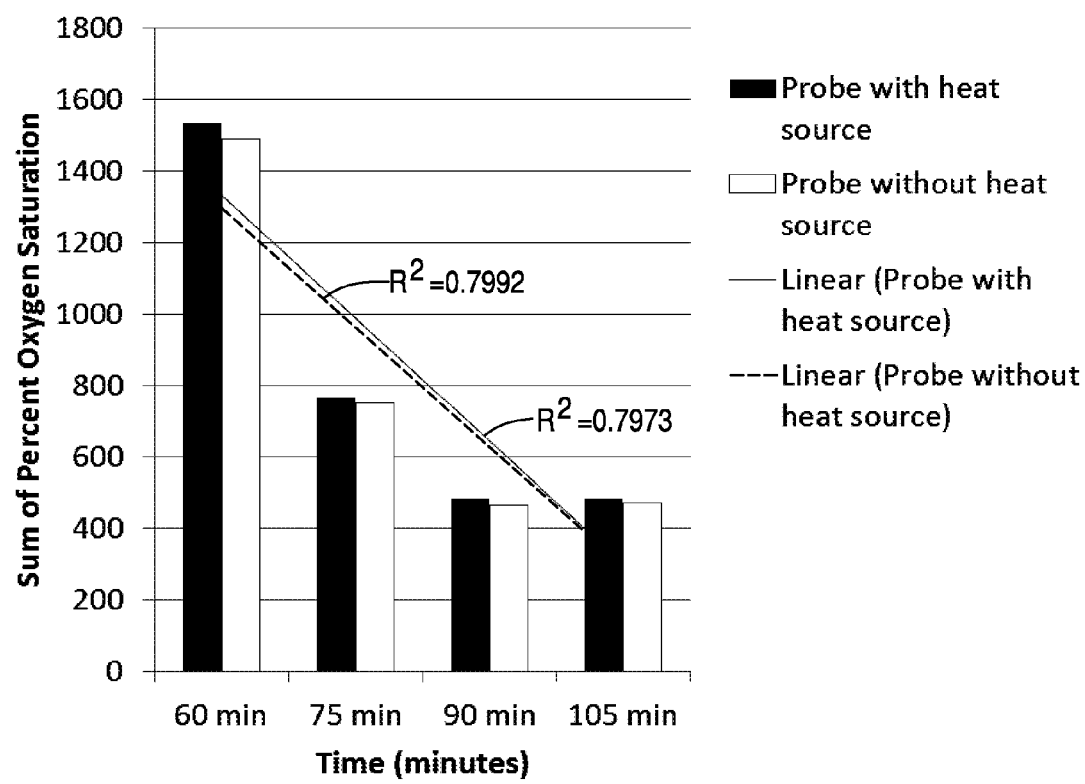
FIG. 11 is a bar chart illustrating $SaO_2$ raw data in control subjects for 60 to 105 minutes.
Figure 12:
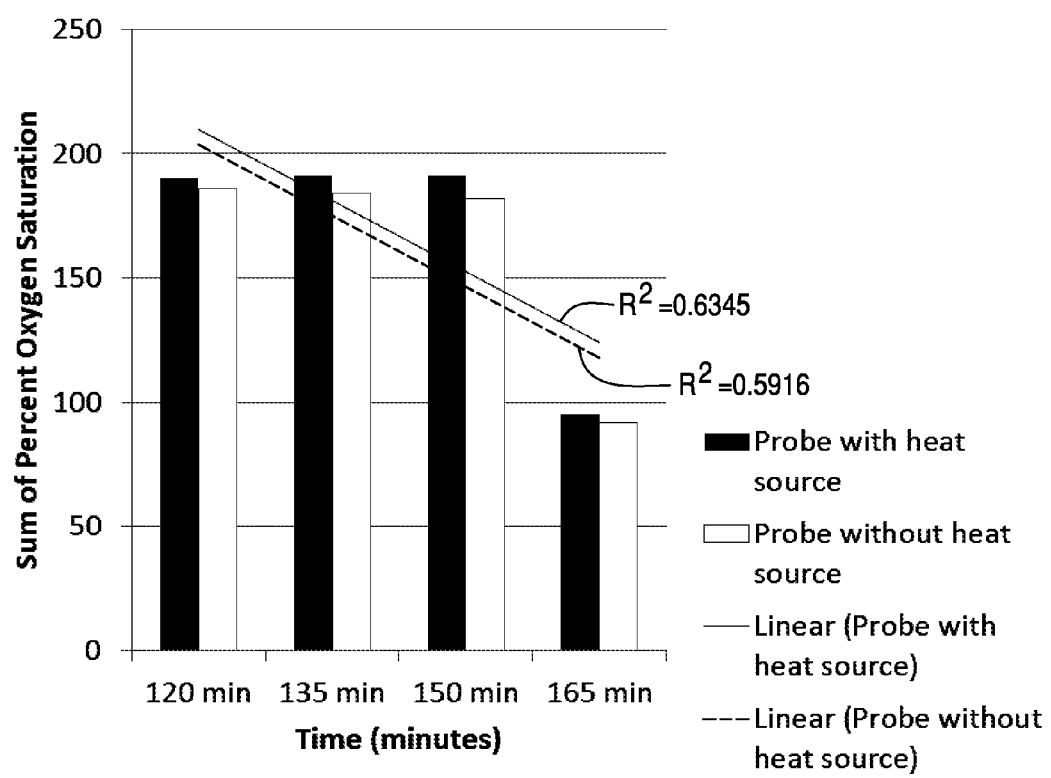
FIG. 12 is a bar chart illustrating $SaO_2$ raw data in control subjects for 120 to 165 minutes.
Figure 13:
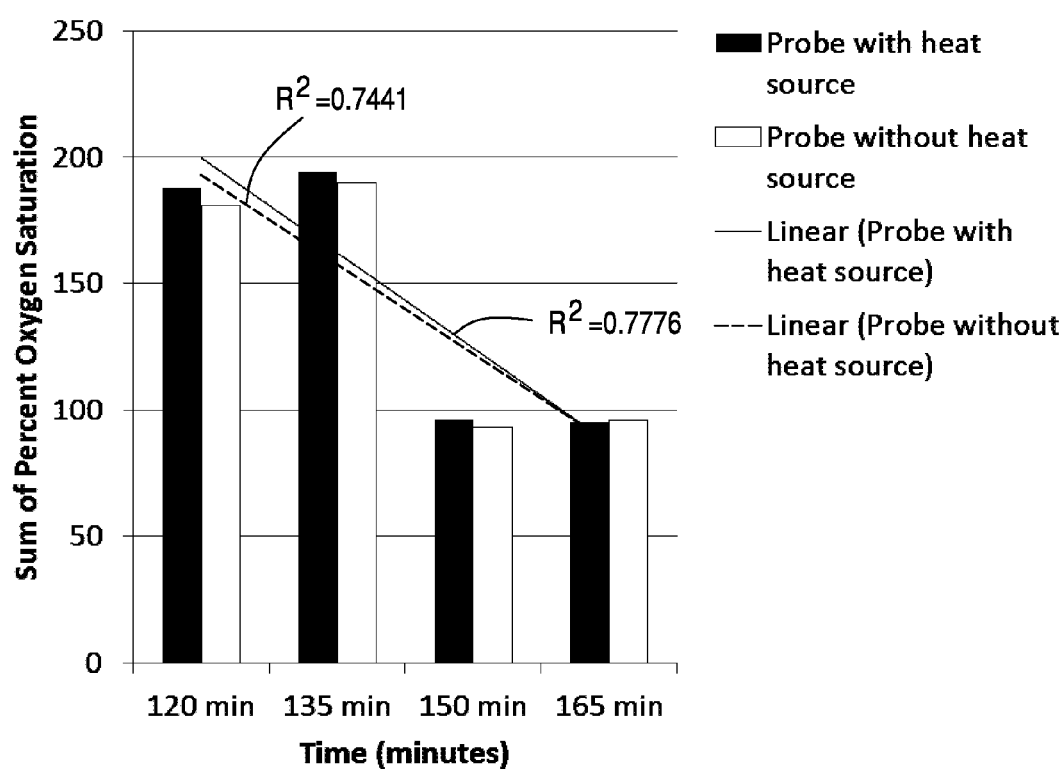
FIG. 13 is a bar chart illustrating $SaO_2$ raw data in test subjects for 120 to 165 minutes.
Figure 14:
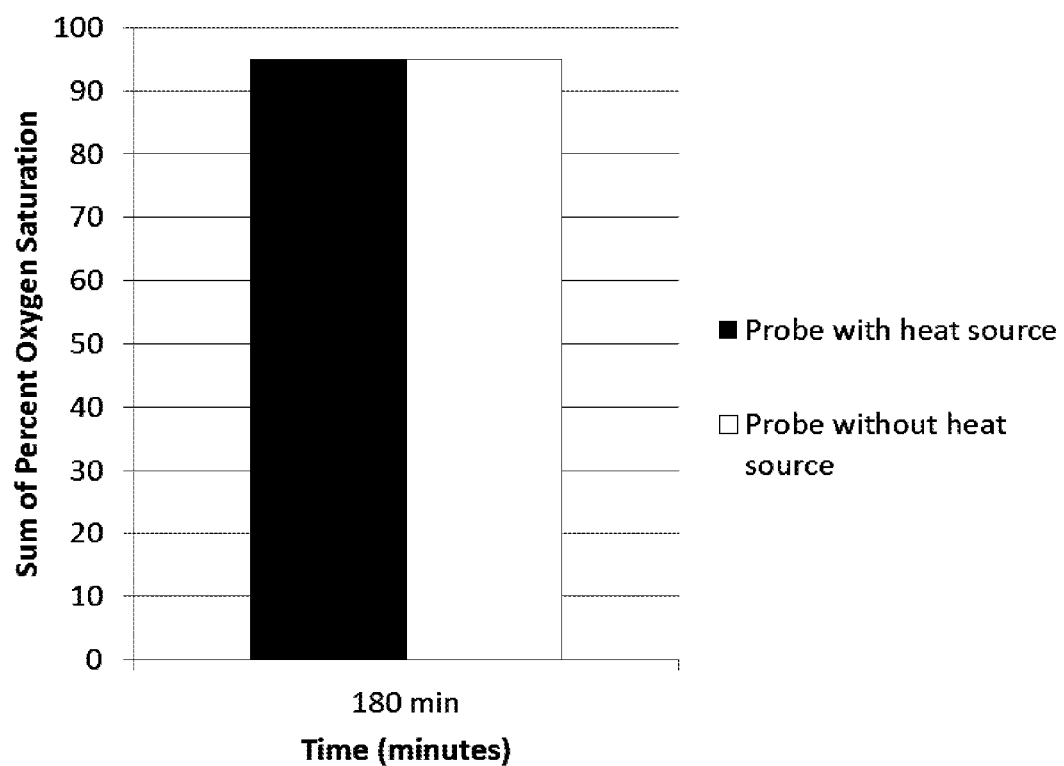
FIG. 14 is a bar chart illustrating $SaO_2$ raw data in test subjects at 180 minutes.

FIG. 4 shows a self-heated pulse oximeter probe 30, according to a second embodiment of the present invention, which is similar to the self-heated oximeter probe 2, except that it includes a strap 32 that is used to secure the closed self-heated pulse oximeter probe 30 onto the patient's index finger 4. The strap 32 may be in replacement of or in addition to other closures, e.g., the adhesive strips 20a and 20b, shown in FIG. 1. Preferably, the strap 32 includes a hook and loop fastener to allow it to reversibly secure the closed self-heated pulse oximeter probe 30 to the finger 4. However, it is within the contemplation/scope of the present invention for strap 32 to employ any other releasable fastening means known in the art, e.g., buttons, adhesives, snaps, ties, etc. Similarly, the adhesive strips 20a and 20b, of self-heated pulse oximeter probe 2, may be replaced by hook and loop fasteners or snaps or other known types of releasable fasteners.

Other harness forms/configurations are also within the contemplation/scope of the present invention. Their common attribute is that they are configured to hold a pulse oximeter probe in a fixed position and to contain a chemical heating source, and are adapted to secure the self-heated pulse oximeter probe to a desired portion of the body, e.g., a finger, ear, heel, forehead, etc. The harness 10 is preferably made from a soft cloth material, such as cotton, but all flexible materials which permit non-irritating securing of the self-heated pulse oximeter probe to the body may be used. Preferably, the harness 10 is made of a single material that is sufficiently breathable to allow an effective amount of air exposure to the chemical heating source during operation. However, the harness 10 may also be made of multiple materials, so long as an air permeable material is used in proximity to the chemical heat source to allow an effective amount of air exposure to the chemical heating source during operation.

The chemical heating source, e.g., chemical heating source 28 (FIG. 3), is preferably an air exposure activated chemical heat source. An example of such a chemical heating source includes a mixture of iron powder, water, salt, activated charcoal and vermiculite. Upon exposure to air, the iron powder begins to oxidize and release heat. The composition of the mixture is selected so that during operation the released heat warms the skin in the region to be heated to a temperature that will enhance the validity of the pulse oximeter and/or pulse rate measurements, but which will not cause burns or tissue damage during the anticipated time of exposure. Also, the composition and the amount of the mixture is selected to produce the desired amount of heat for the desired time of exposure, which may range from a few minutes to several hours.

The chemical heating source is preferably activated by exposure to air. Thus, the chemical heating source is isolated from the air until the self-heated pulse oximeter probe is to be used. The isolation may be done by assembling the self-heated pulse oximeter probe in an inert atmosphere and enclosing it in an air impermeable container, e.g., a plastic bag or other suitable wrapping or enclosure. Another way is to enclose the chemical heating source in an air impermeable container, and to remove the chemical heating source from the container and place it into a pocket of a self-heated pulse oximeter probe harness immediately prior to use.

Preferably, the chemical heating source is provided as a packet including a powder mixture contained in an air permeable sack, which in turn is contained within an air impermeable container, so that immediately prior to use, the air impermeable container may be removed and the packet may be inserted into a pocket of the harness of the self-heated pulse oximeter probe.

The self-heated pulse oximeter probe 2 (or 30) of the present invention is simple to use. For example, immediately prior to use, the air impermeable barrier is removed to activate the chemical heating source by exposing it to air. The self-heated pulse oximeter probe is then positioned so that the pulse oximeter probe is adjacent to the desired measurement location on the body of a person whose $SaO_2$ and/or pulse rate is to be measured. The harness of the self-heating pulse oximeter probe is then secured in place on the person and the lead 8 of the pulse oximeter is functionally connected to a suitable data collection and processing unit. Measurements are then taken for a desired length of time.

Afterwards, the harness 10 is unfastened and the self-heating pulse oximeter probe 2 (or 30) is removed from the person and the lead 8 is disconnected from the data collection and processing unit. If the self-heated pulse oximeter probe is designed for reuse, the chemical heating source (28) is removed from the harness pocket or pockets and properly disposed of. If the self-heated pulse oximeter probe is not designed for reuse, the pulse oximeter probe may be removed, if desired, and the remainder of the self-heated pulse oximeter probe may be properly discarded.

EXAMPLE

A study to test the efficacy of the self-heated pulse oximeter probe of the invention was carried out on 40 subjects. Table 1 (below) lists the details of the subjects at 15 min. intervals for up to three hours of testing. The test subjects were those who suffered from various health issues such as vasoconstriction, peripheral vascular disease, cold extremities, etc., that typically adversely affect obtaining accurate oxygen saturation readings.

TABLE 1

Number of Subjects At Each Interval

| Minutes | Control Subjects | Test Subjects |
|---|---|---|
| 0 | 20 | 20 |
| 15 | 20 | 20 |
| 30 | 20 | 20 |
| 45 | 20 | 20 |
| 60 | 16 | 17 |
| 75 | 8 | 11 |
| 90 | 5 | 7 |
| 105 | 5 | 4 |
| 120 | 2 | 2 |
| 135 | 2 | 2 |
| 150 | 2 | 1 |
| 165 | 1 | 1 |
| 180 | 0 | 1 |

Procedure

Each subject for this study was chosen from the Cathlab schedule; patients scheduled to have a cardiac procedure. Each individual was evaluated to determine if they suffered from any of the health issues, such as vasoconstriction, peripheral vascular disease, or complaints of cold extremities. These individuals were labelled as the "test" subjects. Individuals with none of the above problems were chosen and were considered the normal subjects for the study. These individuals were labelled as the "control" subjects.

Upon arrival at the Cardiac Cathlab, a specialized pulse oximetry probe with external heat pack was applied to each subject on either a finger or toe. The specialized pulse oximetry probe with external heat pack also contained a temperature probe. A second standard of care probe was also attached, as all subjects served as their own controls.

Data collection started with initial readings (time=0 minutes) and every fifteen minutes results were recorded. Data points included temperature of the internal area of the probe (Tables 2 and 3—below), $SaO_2$ (oxygen level), heart rate (Tables 2 and 3—below), adverse events and a pain scale (zero to 10). The time range of each individual study depended on the cardiac procedure. Upon completion of the procedure, the specialized pulse oximetry probe with external heat pack was removed and the subject had completed his/her participation in the study.

TABLE 2

Heart Rate and Probe Temperature for Test Subjects

| Minutes | Heart Rate (Probe With Heat Source) | Heart Rate (Probe Without Heat Source) | Temp. (° C.) (Next to Probe) |
|---|---|---|---|
| 0 | 63.8 | 63.3 | 37.4 |
| 15 | 63.2 | 63.5 | 40.9 |
| 30 | 64.6 | 63.8 | 42.1 |
| 45 | 65.7 | 65.5 | 42.4 |
| 60 | 64.5 | 65.2 | 42.7 |
| 75 | 64.3 | 65.1 | 42.6 |
| 90 | 66.7 | 68.0 | 41.9 |
| 105 | 62.8 | 62.0 | 41.4 |
| 120 | 59.5 | 59.5 | 39.4 |
| 135 | 62.0 | 61.5 | 41.8 |
| 150 | 70.0 | 68.0 | 38.8 |
| 165 | 74.0 | 71.0 | 38.9 |
| 180 | 74.0 | 74.0 | 38.9 |

TABLE 3

Heart Rate and Probe Temperature for Control Subjects

| Minutes | Heart Rate (Probe With Heat Source) | Heart Rate (Probe Without Heat Source) | Temp. (° C.) (Next to Probe) |
|---|---|---|---|
| 0 | 68.2 | 70.7 | 38.3 |
| 15 | 68.5 | 71.2 | 40.5 |
| 30 | 66.9 | 70.0 | 43.0 |
| 45 | 66.6 | 70.1 | 43.0 |
| 60 | 68.0 | 69.3 | 42.9 |
| 75 | 68.8 | 66.5 | 42.7 |
| 90 | 66.2 | 67.4 | 41.4 |
| 105 | 65.0 | 64.4 | 40.9 |
| 120 | 61.0 | 60.5 | 43.6 |
| 135 | 59.0 | 59.0 | 43.5 |
| 150 | 61.5 | 61.5 | 43.8 |
| 165 | 77.0 | 76.0 | 45.0 |

Upon completion of the study, it was determined that the specialized pulse oximetry probe with external heat pack had positive results. There were no complaints regarding the heat source or any pain. The $SaO_2$ readings were found to be consistently higher in the extremity with specialized pulse oximetry probe with external heat pack, for both the control subjects and the test subjects (see FIGS. 5-14).

While this invention has been described as having preferred sequences, ranges, steps, order of steps, materials, structures, shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

What is claimed is:

1. A flexible self-heated pulse oximeter apparatus, comprising:
   a) a flexible harness including first and second sections joined by a bridge section;
   b) a probe removably secured to said bridge section and including a lead for transmitting a signal to a processor;
   c) said harness being adapted to hold said probe in a fixed position relative to a measurement site on the body so as to effectively envelope and position the extremity of the measurement site directly adjacent said probe, and including a pocket in one of said first and second sections thereof;
   d) a self-contained source of chemical heating mixture;

e) said pocket being adapted to accommodate said self-contained source of chemical heating mixture therein; and f) said one of said first and second sections being made of an air permeable material so as to allow the air to come in contact with said chemical heating mixture and release heat.

2. The apparatus of claim 1, wherein:
a) said chemical heating mixture comprises a metal.

3. The apparatus of claim 1, wherein:
a) said chemical heating mixture comprises a metal mixture.

4. The apparatus of claim 3, wherein:
a) the metal mixture comprises iron.

5. The apparatus of claim 3, wherein:
a) the metal mixture comprises iron, activated charcoal, and vermiculite.

6. The apparatus of claim 2, further comprising:
a) an air impermeable container for containing the flexible self-heated pulse oximeter.

7. The apparatus of claim 6, wherein:
a) the metal mixture comprises a disposable mixture.

8. The apparatus of claim 1, wherein:
a) said harness comprises a disposable harness.

9. The apparatus of claim 1, wherein:
a) the air permeable material comprises a cloth material.

10. The apparatus of claim 1, wherein:
a) said probe is adapted to function in transmission or reflectance mode, or both.

11. A non-invasive method of measuring a blood oxygen level (SaO2) or pulse rate of a subject, comprising the steps of:
a) providing a flexible self-heated pulse oximeter apparatus, comprising:
  i) a flexible harness including first and second sections joined by a bridge section;
  ii) a probe removably secured to the bridge section and including a lead for transmitting a signal to a processor;
  iii) the harness being adapted to hold the probe in a fixed position relative to a measurement site on the body so as to effectively envelope and position the extremity of the measurement site directly adjacent the probe, and including a pocket in one of the first and second sections thereof;
  iv) a self-contained source of chemical heating mixture;
  v) the pocket being adapted to accommodate said self-contained source of chemical heating mixture therein; and
  vi) the one of the first and second sections being made of an air permeable material so as to allow the air to come in contact with the chemical heating mixture and release heat;
b) exposing the chemical heating mixture to air;
c) positioning the pulse oximeter apparatus at a measurement site on the subject so as to effectively envelope and position the extremity of the measurement site directly adjacent the probe; and
d) maintaining the pulse oximeter apparatus at the measurement site for a predetermined time period and taking measurements.

12. The method of claim 11, wherein:
the chemical heating mixture comprises a metal mixture.

13. The method of claim 12, wherein:
the metal mixture comprises iron.

14. The method of claim 12, wherein:
the metal mixture comprises iron, activated charcoal, and vermiculite.

* * * * *